United States Patent
Inoue

[19]

[11] Patent Number: 5,891,733
[45] Date of Patent: *Apr. 6, 1999

[54] REAGENT FOR ANALYZING SOLID COMPONENTS IN URINE AND METHOD FOR ANALYZING SOLID COMPONENTS BY EMPLOYING THE SAME

[75] Inventor: Junya Inoue, Ono, Japan

[73] Assignee: Toa Medical Electronics Co., Ltd., Hyogo, Japan

[*] Notice: This patent issued on a continued prosecution application filed under 37 CFR 1.53(d), and is subject to the twenty year patent term provisions of 35 U.S.C. 154(a)(2).

[21] Appl. No.: 545,939

[22] Filed: Oct. 20, 1995

[30] Foreign Application Priority Data

Oct. 20, 1994 [JP] Japan ................... 6-255580

[51] Int. Cl.$^6$ .................................................. G01N 33/48
[52] U.S. Cl. ................... 436/63; 436/8; 436/10; 436/16; 436/17; 436/18; 436/43; 436/52; 436/172
[58] Field of Search .................... 436/8, 10, 16, 436/17, 18, 43, 52, 63, 172; 435/6

[56] References Cited

U.S. PATENT DOCUMENTS

| | | |
|---|---|---|
| 3,961,039 | 6/1976 | Sternheimer . |
| 4,193,980 | 3/1980 | Clason et al. ................ 424/3 |
| 4,331,759 | 5/1982 | Giannini et al. ............ 435/4 |
| 4,400,370 | 8/1983 | Kass ............................ 424/3 |
| 4,581,223 | 4/1986 | Kass ............................ 424/3 |
| 4,622,298 | 11/1986 | Mansour et al. . |
| 4,751,188 | 6/1988 | Valet .......................... 436/63 |
| 4,810,487 | 3/1989 | Kass ............................ 424/3 |
| 5,057,413 | 10/1991 | Terstappen et al. ......... 435/6 |
| 5,350,695 | 9/1994 | Colella et al. ............. 436/63 |
| 5,407,794 | 4/1995 | Kass ........................... 436/63 |

FOREIGN PATENT DOCUMENTS

| | | |
|---|---|---|
| 0 106 339 A3 | 4/1984 | European Pat. Off. . |
| 120396 | 10/1984 | European Pat. Off. . |
| 0 162 607 | 11/1985 | European Pat. Off. . |
| 0 226 272 | 6/1987 | European Pat. Off. . |
| 266 194 | 5/1988 | European Pat. Off. . |
| 333560 | 9/1989 | European Pat. Off. . |
| 485945 | 5/1992 | European Pat. Off. . |
| 0 513 762 A1 | 11/1992 | European Pat. Off. . |
| 0 525 398 A3 | 2/1993 | European Pat. Off. . |
| 0 545 314 A1 | 6/1993 | European Pat. Off. . |
| 0 613 003 A1 | 8/1994 | European Pat. Off. . |
| 63-70166 | 3/1988 | Japan . |
| 2-187661 | 7/1990 | Japan . |
| 4-184168 | 7/1992 | Japan . |
| 4-337459 | 11/1992 | Japan . |
| 2026015 | 1/1980 | United Kingdom . |
| 2 059 582 | 4/1981 | United Kingdom . |
| 2074340 | 10/1981 | United Kingdom . |

OTHER PUBLICATIONS

M. Hejtmanek et al. *Chem. Abstr.* 1991, 114, 181527t.
M.R.G. O'Garman et al. *Chem. Abstr.* 1992, 116, 79772y.
K.J. Hutter *Chem. Abstr.* 1992, 117, 68572c.
L.G. Lee et al. *Chem. Abstr.* 1987, 106, 115946n.
Peter Jay Sims et al., Studies on the mechanism . . . , Biochemistry, vol. 13, No. 16, 1974, pp. 3315–3330.
M. Nakanishi, A new stain for urinary sediments, Chemical Abstracts, vol. 116, No. 116, No. 25, Jun. 22, 1992.

*Primary Examiner*—Arlen Soderquist
*Attorney, Agent, or Firm*—Birch, Stewart, Kolasch & Birch, LLP

[57] ABSTRACT

A reagent for analyzing solid components in urine comprising: (i) a buffer agent for maintaining pH at 5.0 to 9.0, (ii) an osmotic pressure compensating agent for maintaining osmotic pressure at 100 mOsm/kg to 600 mOsm/kg, (iii) a first dye which is a condensed benzene derivative, (iv) a second fluorescent dye capable of staining a damaged cell, and (v) a chelating agent.

20 Claims, 7 Drawing Sheets

REAGENT FOR ANALYZING SOLID COMPONENTS IN URINE AND METHOD FOR ANALYZING SOLID COMPONENTS BY EMPLOYING THE SAME

BACKGROUND OF THE INVENTION

1. Field of the Invention

The present invention relates to a reagent for analyzing solid components in urine and to a method for analyzing solid components in urine employing the reagent, and more particularly to a reagent employed for an optical analysis of solid components in urine by applying flow cytometry and a method for analyzing the same.

2. Related Art

In renal and urinary diseases such as infectious diseases, inflammatory lesions, degenerative lesion, calculosis, tumor and the like, various kinds of solid components appear in the urine depending on the disease. Examples of solid components include erythrocytes, leukocytes, epithelial cells, urinary casts, bacteria, fungi, crystals and mucus threads. Analyzing these components in urine is of great importance for early discovery of renal and urinary diseases and presumption of abnormal sites. For example, the measurement of erythrocytes is important in determining whether there is bleeding in the passageway from the nephric glomerulus to urethra. Appearance of leukocytes suggests suspicion about renal disease such as pyelonephritis, leading to early discovery of inflammation and infectious disease. By investigating urinary casts and morphological features of erythrocytes, the derivational sites thereof can also be inferred.

Conventionally, solid components in urine have been analyzed by visual microscopy using a microscope. This is performed by concentrating the urine to be tested by centrifugalization, then sometimes after staining the obtained sediments, putting them on a microscope slide so as to classify and count them under a microscope.

In recent years, an automatic measuring apparatus has been developed in which a flat sheath flow and an image processing technique are combined. The urine sample adjusted to flow in an extremely flat stream with a sheath liquid serving as an outer layer is filmed by a video recorder and the still picture thus obtained is subjected to image processing, thereby cutting out and displaying the images of solid components in the sample liquid. Observing the display, an examiner distinguishes and counts the solid components contained therein.

Further, for automatically classifying and counting the solid components in urine, Japanese Unexamined Patent Publication No. Hei 4(1992)-337459 discloses a reagent (employed) for an analysis of cells in urine by applying flow cytometry and a method for analyzing thereof. The reagent employed therein contains a fluorescent dye, an osmotic pressure compensating agent and a buffer agent. Various kinds of fluorescent dyes, osmotic pressure compensating agents and buffer agents are disclosed therein and a reagent employing Neutral Red or Auramine O as a fluorescent dye is described in an Embodiment.

Incidentally, it is desired to test the urine specimen as soon as possible after the specimen is taken out from the subject because the solid components degenerate and the number of bacteria increases in accordance with the passage of time.

Visual microscopy by microscope requires a lot of time and operation for the pretreatment of the urine specimen such as centrifugalization and concentration. Besides, microscopy is a great burden to the examiner. Also, the microscopy accuracy is low because the number of observed cells are small.

An automatic measuring apparatus using an image processing technique is advantageous to microscopy because the burden of microscopy is alleviated. However, when a lot of specimens are to be tested, it is not satisfactory enough because solid components need to be distinguished by an examiner and the processing speed is not speedy.

Moreover, distinguishing the solid components requires skill in both visual microscopy and examination by an automatic measuring apparatus using an image processing technique.

A method disclosed in Japanese Unexamined Patent Publication No. Hei 4(1992)-337459 wherein flow cytometry is applied to urine analysis have the advantage of quick measurement. However, on further investigation, the method was found to have the following problems.

(1) Appearance of crystals in the urine renders it difficult to distinguish between the crystals and the erythrocytes contained therein.

(2) When a lot of amorphous salts appear in the specimen, it becomes difficult to classify the other cells.

(3) In measuring a urine specimen containing hemoglobin or protein by using the reagent containing Auramine O having pH 8.5 shown in an Example of Japanese Unexamined Patent Publication No. Hei 4(1992)-337459, it may be impossible to measure the urine specimen accurately because of bonding the hemoglobin or the protein to the dye and depositing tiny sediments.

(4) Although the problem of (3) is solved by allowing the pH to be set at an acid value, stainability of the reagent declines at such pH value and, when yeast-like fungi appear in the specimen, it is difficult to distinguish erythrocytes from the fungi.

(5) When urine is analyzed by flow cytometry, it is necessary to repress the dilution ratio to be low because the quantity of solid components contained in the urine is small. However, when the dilution ratio is low and a fluorescent substance, for example, a pharmaceutical agent such as a vitamin or an antibiotic substance is excreted in the urine, it may be difficult to obtain sufficient fluorescent signal intensity of the solid components contained therein because the background fluorescence (background noise) of the urine itself is not negligible. When Neutral Red is used, there will be a great influence of the background fluorescence caused by the dye which does not bond to the cells.

SUMMARY OF THE INVENTION

The present invention provides a reagent for analyzing solid components in urine comprising: (i) a buffer agent for maintaining pH at 5.0 to 9.0, (ii) an osmotic pressure compensating agent for maintaining osmotic pressure at 100 mOsm/kg to 600 mOsm/kg, (iii) a first dye which is a condensed benzene derivative, (iv) a second fluorescent dye capable of staining a damaged cell, and (v) a chelating agent.

Further, the present invention provides a reagent for analyzing solid components in urine comprising: (I) a buffer agent for maintaining pH at 5.0 to 9.0, (II) an osmotic pressure compensating agent for maintaining osmotic pressure at 100 mOsm/kg to 600 mOsm/kg, (III) a dye capable of being excited by a red wavelength light, and (IV) a chelating agent.

In another aspect, the present invention provides a method for analyzing solid components in urine by mixing the urine with either of the above reagents to stain the desired solid components in the urine, applying an excitation light to solid components in the above stained urine and measuring the scattered light and the fluorescent light emitted from the solid components.

DESCRIPTION OF THE PREFERRED EMBODIMENTS

Figure 1:
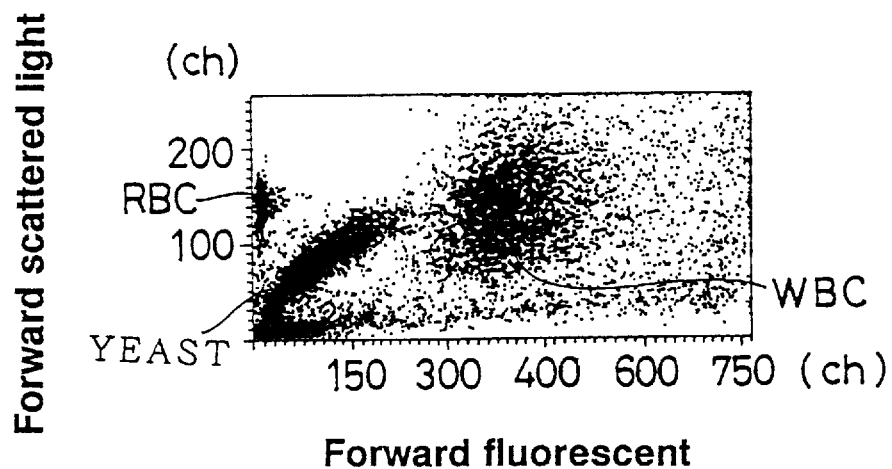
FIG. 1 is a scattergram obtained by measuring the forward scattered light and the forward fluorescent light when solid components in urine are stained by employing the reagent for analyzing solid components in urine according to the present invention.

Examples of solid components in urine that are to be measured according to the present invention include, especially, erythrocytes, leukocytes, epithelial cells, urinary casts, bacteria and yeast-like fungi.

The buffer agent in the analyzing reagent of the present invention may be used to maintain within a certain pH range being able to obtain a stable fluorescence intensity of the specimen to be measured. The pH value may be adjusted to be within the range of pH 5.0 to 9.0 in order to prevent hemolysis of erythrocytes. Among crystalline components contained in urine, especially amorphous salt can be dissolved by dilution with an aqueous solution such as a physiological saline solution, a dilute hydrochloric acid, a dilute acetic acid, an aqueous solution of potassium hydroxide. However, some of the crystalline components contained in urine precipitate in an acidic solution and others precipitate in an alkaline solution. Therefore, pH value of 6.5 to 7.5 is preferable and pH value of 6.8 to 7.2 is more preferable because amorphous salts precipitating in an acidic or alkaline solution are more rapidly dissolved at around neutral. As buffer agents, a conventional known one may be used. For example, a Good's buffer agent such as Tris and MES, Bis-Tris, ADA, PIPES, ACES, MOPSO, BES, MOPS, TES, HEPES, DIPSO, TAPSO, POPSO, HEPPSO, EPPS, Tricine, Bicine and Taps may be used. Among these, HEPES is preferable. The concentration is controlled depending on the buffer capacity of the buffer agent to be used so that the pH value remains within a certain range when the urine specimen is diluted. Generally, the concentration is 20 to 500 mM, preferably 50 to 200 mM.

The osmotic pressure compensating agent may be added for preventing hemolysis of erythrocytes and obtaining a stable fluorescence intensity. The osmotic pressure of urine is distributed widely from 50 to 1300 mOsm/kg. When the osmotic pressure of analyzing agent is too low, hemolysis of erythrocytes proceeds at an early stage. When it is too high, cells are much damaged. Therefore, the osmotic pressure preferably is 100 to 600 mOsm/kg, more preferably 150 to 500 mOsm/kg. As an osmotic pressure compensating agent, an inorganic salt, an organic salt such as a propionate or a sugar may be used. Examples of inorganic salts comprise sodium chloride, potassium chloride, lithium chloride or the like. Examples of propionates comprise sodium propionate, potassium propionate, ammonium propionate or the like. Examples of other organic salts comprise oxalate, acetate or the like. Examples of sugars comprise sorbitol, glucose, mannitol or the like.

As for the first dye, a condensed benzene derivative may be used such as represented by the following formula:

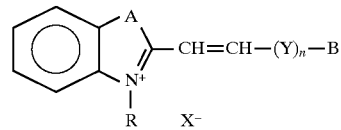

wherein A is —O—, —S— or —C(CH$_3$)$_2$—, R is a lower alkyl group, X is a halogen, Y is —CH= or —NH—, n is 0 or 1; and B is represented by the following formula:

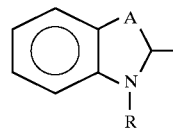

wherein A and R have the same meaning as the above, or a phenyl group substituted by two lower alkoxy groups or by a di-(lower alkyl)amino group (wherein the lower alkyl may be optionally substituted by a cyano group).

The above lower alkyl group means an alkyl group with 1 to 6 carbon atoms, examples of which are methyl, ethyl propyl, butyl, isobutyl, pentyl and hexyl. Examples of halogen atom X include fluorine, chlorine, bromine and iodine. The phenyl group substituted by two lower alkoxy groups of B means a phenyl group substituted by two $C_{1-3}$ alkoxy groups, preferably by two $C_{1-2}$ alkoxy groups such as methoxy group and ethoxy group. Examples are 2,6-dimethoxyphenyl and 2,6-diethoxyphenyl. The phenyl group substituted by a di-(lower alkyl)amino group (wherein the lower alkyl may be optionally substituted by a cyano group) of B means a phenyl group substituted by a di-$C_{1-3}$ alkylamino group, preferably by a di-$C_{1-2}$ alkylamino group. Here, the alkyl group may be optionally substituted by a cyano group. Examples of the alkyl are methyl, ethyl, cyanomethyl and cyanoethyl. Examples of the phenyl group substituted by a di-(lower alkyl)amino group (wherein the lower alkyl may be optionally substituted by a cyano group) is a group such as 4-dimethylaminophenyl, 4-diethylaminophenyl and 4-(cyanoethylmethylamino) phenyl.

Examples of these condensed benzene derivative are:

3,3'-diethyl-2,2'-oxacarbocyanine iodide (NK-85, obtained from: Nippon Kankoh Shikiso Kenkyusho Co., Ltd. [All the following NK-series are obtained from the above company], DiOC2(3))

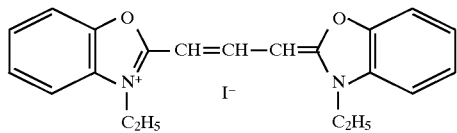

2-(p-dimethylaminostyryl)-3-ethylbenzothiazolium iodide (NK-91)

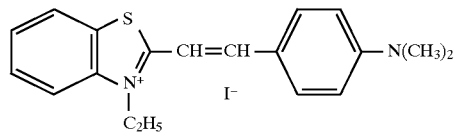

3,3'-dimethyl-2,2'-oxacarbocyanine iodide (NK-86, DiOC1(3))

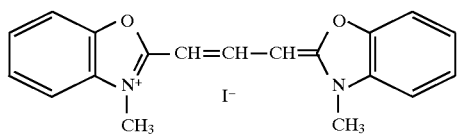

3,3'-(di-n-propyl)-2,2'-oxacarbocyanine iodide (NK-2605, DiOC3(3))

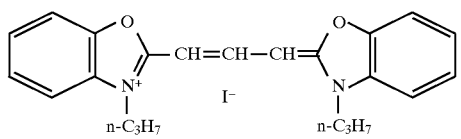

3,3'-(di-n-pentyl)-2,2'-oxacarbocyanine iodide (NK-2453, DiOC5(3))

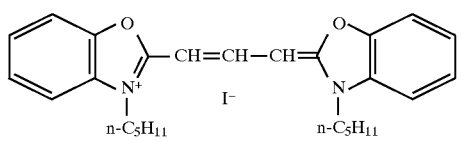

3,3'-(di-n-hexyl)-2,2'-oxacarbocyanine iodide (NK-2280, DiOC6(3))

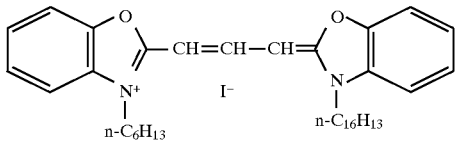

2-(p-dimethylaminostyryl)-3-methylbenzooxazolium iodide (NK-528)

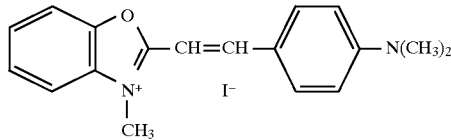

2-(p-dimethylaminostyryl)-1,3,3-trimethyl-3H-indolium iodide (NK-97)

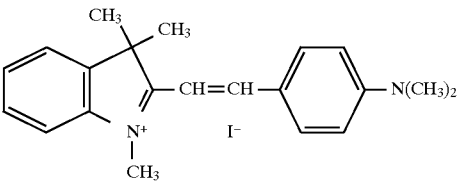

Basic Yellow 11

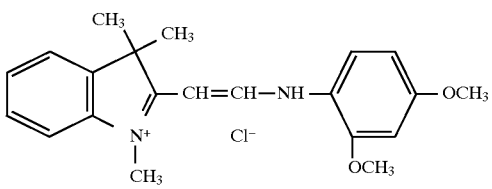

Basic Red 14

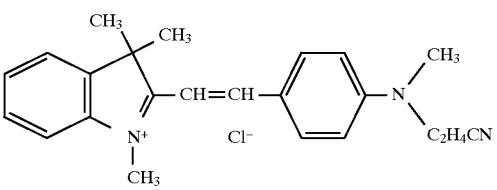

among which DiOCn(3) (n=1 to 6) of oxacarbocyanine dye are preferable and DiOC6(3) is more preferable. The first dye to be used is not specifically limited to the above-described compounds. Any dye may be used as long as it has an optimal dyeing pH value at pH 5.0 to 9.0, preferably at pH 6.5 to 7.5 and bonds to cell membrane but does not precipitate by bonding to urinary components such as protein. Concentration of the first dye is adjusted so that the final concentration (concentration of the dye in the specimen to be measured) is within the range of 1 to 30 ppm, among which 5 to 20 ppm is preferable.

As for the second fluorescent dye, a dye capable of staining a damaged cell, for example, EB (ethidium bromide) or PI (propidium iodide) may be used. Preferably, EB is used. Concentration of the second fluorescent dye is adjusted so that the final concentration is within the range of 1 to 100 ppm, among which 30 to 60 ppm is preferable.

When the first dye and the second dye are used in mixture, a blue wavelength light may be used as an excitation light source.

Alternatively, in the present invention, dyes capable of being excited by a red wavelength light may be used instead of using the above first dye and the second fluorescent dye in mixture. In such a case, the dye for analysis may be prepared by using one dye or mixing two or more dyes selected from the group consisting of:

NK-321

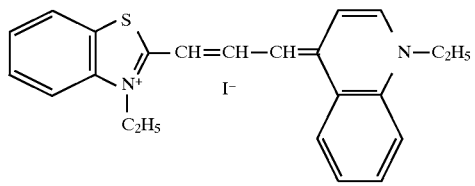

NK-1590

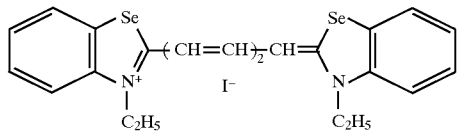

NK-529

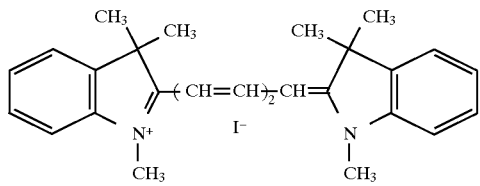

NK-2782

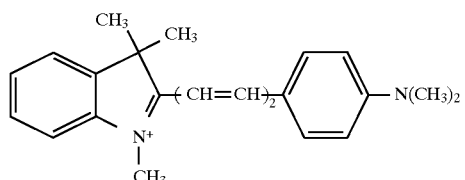

Oxazine 4

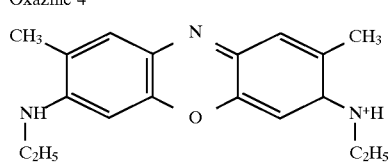

NK-138

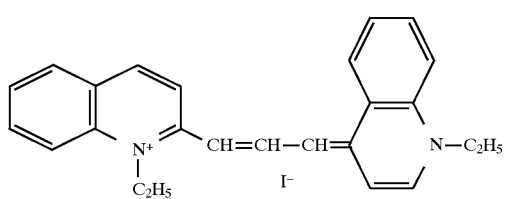

Basic Green

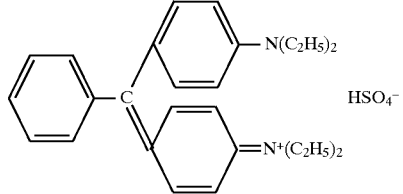

Capri Blue GON

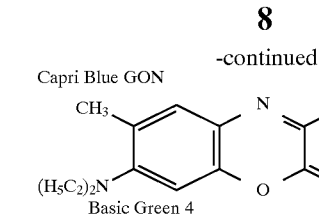

Basic Green 4

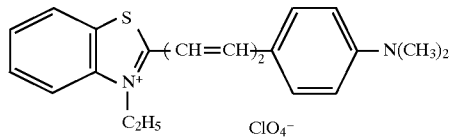

NK-2783

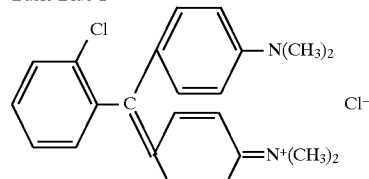

Basic Blue 1

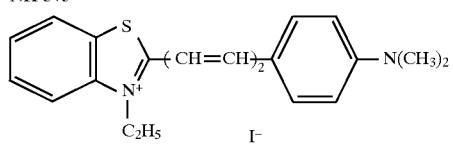

NK-375

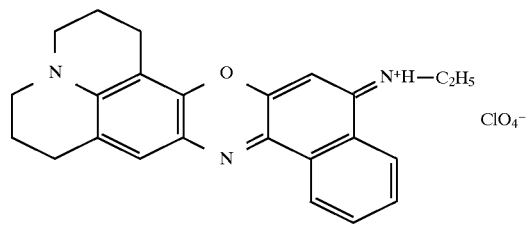

Oxazine 750 perchlorate

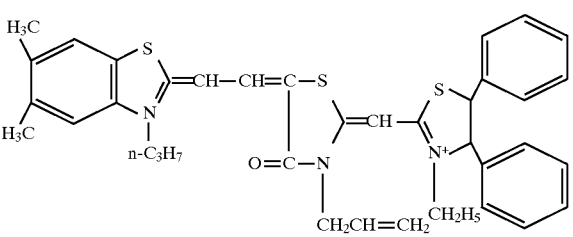

NK-1954

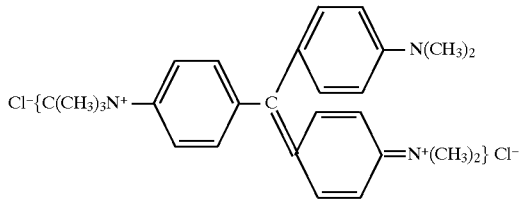

Basic Blue 20

Basic Blue 24
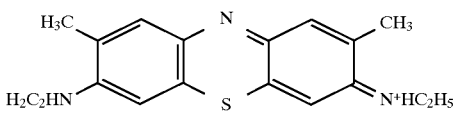

Oxazine 720
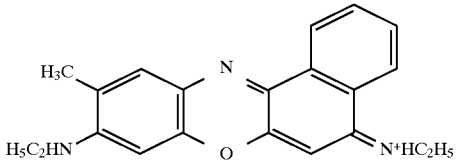

NK-1836
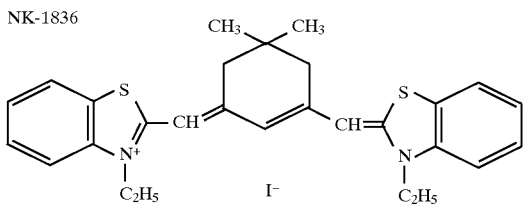

NK-136
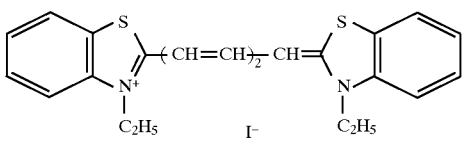

NILE blue chloride
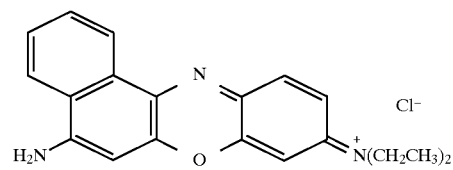

NK-1511
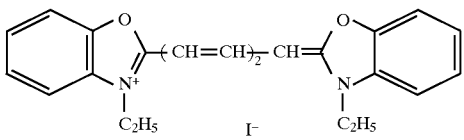

NK-376
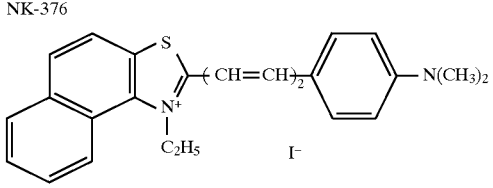

NK-2711
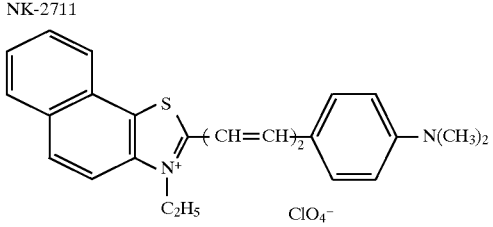

Iodine Green
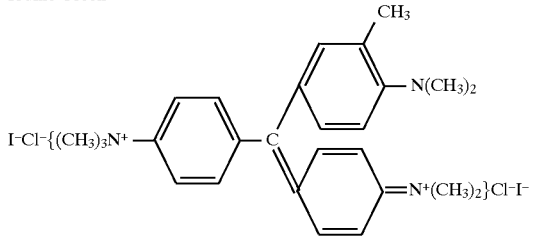

NK-96
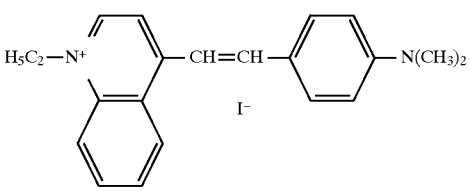

Rhodnile Blue,
Capri Blue BB,
Basic Blue 124 and
Basic Blue 1.

In the above dye, NK-series may be obtained from Nippon Kankoh Shikiso Kenkyusho Co., Ltd.; Oxazine 4, Oxazine 750 perchlorate and Oxazine 720 may be obtained from Exciton, Inc.; Basic Green and Iodine Green may be obtained from E. Merck Darmstadt.; Capri Blue GON may be obtained from Tokyo Kasei Kogyo Industry Co., Ltd.; Nile Blue chloride may be obtained from Nacarai Tesque, Inc.; Rhodnile Blue may be obtained from Aldrich Chemical Company Inc.; and Capri Blue BB may be obtained from Chloma Gesellshaft Schmid & Co. The concentration of the dye is adjusted so that the final concentration can be used within the range of 1 to 300 ppm, among which 5 to 100 ppm is preferable.

The chelating agent may be used for dissolving amorphous salts (for example, ammonium magnesium phosphate, calcium carbonate) appearing in urine. Any kind of agent may be used as long as it is a decalcifying or demagnesifying agent. For example, EDTA salt, CyDTA, DHEG, DPTA-OH, EDDA, EDDP, GEDTA, HDTA, HIDA, Methyl-EDTA, NTA, NTP, NTPO or EDDPO may be used. Preferably, EDTA salt, CyDTA or GEDTA is used. The concentration of the chelating agent may be used within the range of 0.05 to 5 W/W %, preferably 0.1 to 1 W/W %. Here, th& decalcifying or demagnesifying agent means an agent capable of bonding to with calcium and magnesium ions to form water soluble compounds.

The reagent according to the present invention may consist of one solution containing the buffer agent, the osmotic pressure compensating agent, the dyes and the chelating agent. Alternatively, the reagent may consist of two solutions wherein one is a dyeing solution containing the dyes and the other is a diluent solution containing the buffer agent, the osmotic pressure compensating agent and the chelating agent.

When the reagent consists of two solutions, namely, a dyeing solution and a diluent solution, stability in preserving the dyeing solution can be improved by dissolving the dyes into a water soluble organic solvent, because dyes are often unstable in an aqueous solution. The dyeing solution may further comprise a stabilizing agent for these dyes. A water soluble organic solvent that can be used in this case is, preferably, a lower alkanol, a lower alkylene glycol or a lower alkylene glycol-mono-lower alkyl ether. For example, methanol, ethanol, n-propanol, ethylene glycol, diethylene glycol, triethylene glycol, ethylene glycol-mono-methyl ether or ethylene glycol-mono-ethyl ether may be used. Among these, ethylene glycol, diethylene glycol and triethylene glycol are preferable. Considering the influence on cells in urine and the viscosity, ethylene glycol is the most preferable. The diluent solution may also comprise an antibacterial agent so as to prevent proliferation of bacteria during a long-term preservation. Antibacterial agents to be used are not specifically limited. A triazine antibacterial agent, a thiazole antibacterial agent such as BIT (benzisothiazolone) and a pyridine antibacterial agent such as PTO (pyrithione) may be used. Antibacterial agent may be added at a reasonable concentration which does not have a bad influence on the measuring system. The above-mentioned stabilizing agent and antibacterial agent may be added to the reagent consisting of one solution.

Conveniently, the electric conductivity of the reagent according to the present invention is adjusted to be within the range of 1 to 10 mS/cm, preferably 4 to 7 mS/cm for detecting urinary casts by measuring the electric resistance signal. When the buffer agent or the osmotic pressure compensating agent have a high degree of electrolytic dissociation, adjusting the electric conductivity to within the above range lowers the osmotic pressure, which may cause hemolysis of erythrocytes in urine. However, by using an organic acid as the buffer agent or by using an organic salt or a nonelectrolyte (such as a sugar) as an osmotic pressure compensating agent or by appropriately combining the above two agents, the osmotic pressure can be desirably raised while preventing the rise of the electric conductivity.

In analyzing solid components in urine with the reagent of the present invention, the original urine is mixed with the reagent.

By using a reagent which consists of one solution containing the components (i) to (v) or (I) to (IV), the original urine is diluted 2 to 20 times by mixing and the solid components contained in the urine are stained. The dilution ratio of the original urine is preferably 2 to 16 times, especially 4 to 10 times. Here, the above reagent is preferably warmed at 30° to 40° C., desirably 33° to 37° C. in advance so as to rapidly dissolve amorphous salts contained in the urine. It is desirable to mix the original urine with the reagent in the range of room temperature to 40° C., preferably 33° to 37° C. for 5 to 60 seconds, preferably 10 to 30 seconds. If the reagent consists of two solutions, namely, a dyeing solution and a diluent solution, the original urine is added after the dyeing solution is mixed with the diluent solution or, alternatively, the dyeing solution is added after the urine is mixed with the diluent solution. In the case of the reagent consisting two solutions, the final dilution ratio of the urine is preferably 4 to 10 times. Also, the diluent solution is preferably warmed at 30° to 40° C., desirably 33° to 37° C. in advance so as to rapidly dissolve amorphous salts contained in the urine.

Figure 6:
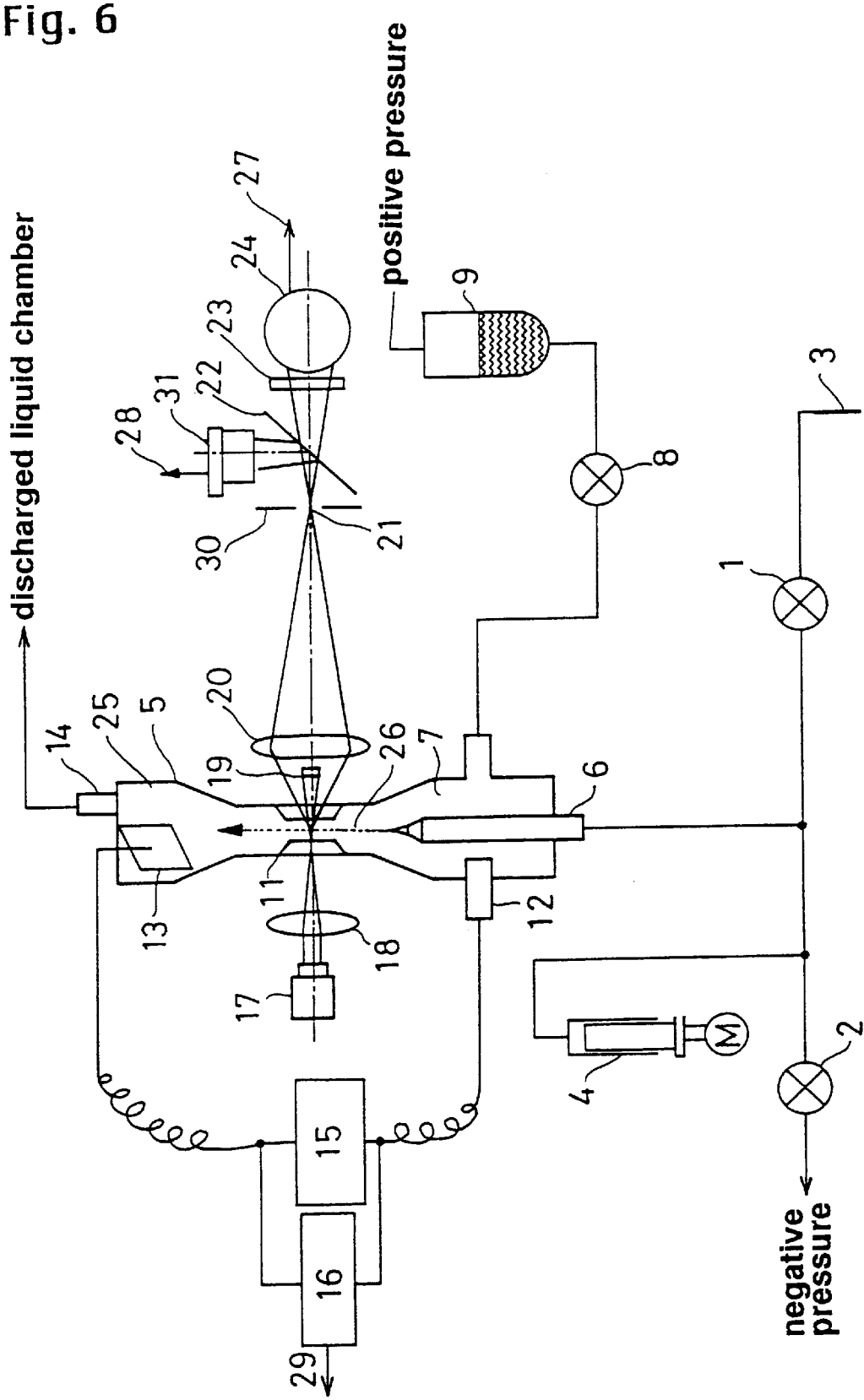
FIG. 6 is a schematic model view illustrating a flow cytometer preferably used for measuring solid components in urine by employing the reagent for analyzing solid components in urine according to the present invention.

The urine thus mixed with the above reagent is let to run through a flow cell as a urine specimen. Then, an excitation light is applied to the urine specimen running through the flow cell for measuring the intensities of the forward scattered light and fluorescent light emitted from the solid components in the urine specimen. In this way, the solid components contained in urine can be analyzed. In case of measuring urinary casts, it is desirable to measure the electric resistance signal intensity (volume information) of the urine-specimen as well because it would increase the detection-sensitivity of casts. Therefore, it is desirable that the method of analyzing urine according to the present invention employs a flow cytometer capable of measuring both the electric resistance signal and the optical information. An example of flow cytometer which is suitable for use in the present invention is shown in FIG. 6.

First, by opening the valves 1 and 2 for a certain period of time, the sample liquid is introduced from the suction nozzle 3 by negative pressure of the exhaust liquid chamber and fills the valves 1 and 2. The sample liquid is ejected from the sample nozzle 6 by operation of the syringe 4 forcing out the liquid with a constant flow rate. At the same time, a sheath liquid is supplied into the chamber 7 in the flow cell 5 by opening the valve 8. By this process, the sample is narrowed down along the inside surface of the chamber 7 to form a sheath flow and passes through the orifice 11 as shown in FIG. 6. The shape of the orifice 11 is prismatic, the length of each inner side being 100 to 300 $\mu$m. The orifice 11 is made of optical glass (including quartz glass). The sheath flow thus formed enables the particles to flow one by one arranged in a line through the center of the orifice 11. The sample liquid and the sheath liquid that have passed through the orifice 11 are discharged through the collector tube 14 secured to the chamber 25.

The electrode 13 made of platinum is provided inside the chamber 25 and serves as a positive electrode. The electrode 12 made of stainless steel is provided inside the chamber 7 and serves as a negative electrode. The electric resistance between the electrodes 12 and 13 are determined by the resistivity (electric conductivity) of the sheath liquid, the hole dimension (hole cross section), hole length of the orifice, the resistivity of the sample liquid and the diameter of the flowing sample liquid.

The power source 15 is supplied a constant direct current between the electrodes 12 and 13. Providing a constant direct current between the electrodes 12 and 13 generates a direct current voltage determined by the electric resistance and the magnitude of the electric current between the electrodes 12 and 13. When particles pass through the orifice 11, the electric resistance between the ends of the orifice 11 changes. Thus, while the particles are passing, the voltage generated between the electrodes 12 and 13 increase. Also, a pulse-like voltage is generated in proportion to the size of the particles passing through the orifice 11. Therefore, this voltage is added to the above direct current voltage and the resulting voltage appears between the electrodes 12 and 13. This is detected by an amplifier 16, producing a resistance signal 29 as an output.

A laser light irradiated from a laser 17 is narrowed down to have an elliptic shape by a condenser lens 18 and is applied to the sample flow 26 generally at the center of the orifice 11. The shape of the laser light is as follows. The length thereof along the sample flow is about the same as the particle diameter of the blood cells, for example, as narrow as about 10 $\mu$m. The length along the direction perpendicular to both the sample flow and the optical axis of the applied light is considerably greater than the particle diameter of the blood cells, for example, about 150 to 300 $\mu$m. Some of the laser light applied to the sample flow 26 does not hit the cells (solid components) and is transmitted through the flow cell 5. This transmitted light is interrupted by a beam stopper 19. The other light applied to the sample flow 26 hits the cells, producing a forward scattered light and a forward fluorescent light in a narrow range of angles. The forward scattered light and fluorescent light are collected by a collector lens 20 and then pass through the pinhole 21 of the shield 30 to reach the dichroic mirror 22. Having a wavelength longer than that of the scattered light, the fluorescent light is transmitted through the dichroic mirror 22 in a high transmittance ratio. After scattered light is further removed by a filter 23, the fluorescent light is detected by a photomultiplier tube (PMT) 24 and transformed to electric signals 27 for output. The scattered light is reflected by the dichroic mirror 22 and received by a photodiode 31 to be transformed to electric signals 28 for output.

The reagent of the present invention for analyzing solid components in urine provides an effect that, by mixing the reagent with urine, amorphous salts are dissolved and the solid components in urine are stained so as to classify suitably.

Generally, most of amorphous salts often observed in urinary sediments are phosphates and urates. Most of the phosphates are calcium salts and, by adding a chelating agent, the calcium salts form water soluble chelate compounds to be dissolved. Urates are dissolved by dilution and warming. These amorphous salts are observed also in urine of a normal human being and are of low clinical significance. Therefore, in order to accurately detect other clinically significant solid components (erythrocytes, leukocytes, bacteria, yeast-like fungi, urinary casts, and others), it is necessary to dissolve amorphous salts. However, large crystals and calcium oxalate are slow to dissolve even by addition of a chelating agent or by heating treatment and some of them remain undissolved when the measurement by flow cytometry is conducted. Moreover, morbid crystals such as cystine, leucine, tyrosine, cholesterin and 2,8DHA are not easily dissolved even by these operations. Due to this reason, the remaining crystals overlap the erythrocyte domain, sometimes rendering it difficult to accurately measure the erythrocytes. Therefore, it is especially necessary to strongly stain erythrocytes so that these crystals do not have a bad influence on the measurement of other solid components.

Meanwhile, the fluorescence intensity exhibited by solid components in urine varies in a wide range from a weak one to a strong one depending on the kind of solid components. For example, the fluorescence intensity of erythrocytes is much weaker than that of leukocytes. So far, in case of measuring leukocytes in blood, it was not necessary to pay so much attention to erythrocytes or background fluorescence exhibiting only an extremely weak fluorescence intensity, because leukocytes are strongly stained. However, in analyzing solid components in urine, it is necessary to detect substances such as erythrocytes exhibiting only a weak fluorescence intensity. In order to achieve this, the detector (PMT) sensitivity needs to be adjusted higher than in the case of measuring leukocytes in blood. However, raising the sensitivity of detector brings a bad influence due to background fluorescence from urine itself or background fluorescence from fluorescent dyes that does not bond to cells, so that it was sometimes difficult to obtain a sufficient fluorescence signal intensity from erythrocytes to make measurements thereof.

Through research, the present inventor has found out that the above problems can be solved by using a fluorescent dye such as DiOCn(3) (n=1 to 6) capable of staining cell membrane of erythrocytes.

The first dye, especially, DiOCn(3) (n=1 to 6) bonds, by ionic bonding, to all kinds of cell membranes, nuclei and granules. On the other hand, Auramine O as described by an Example in the specification of Japanese Unexamined Patent Publication No. Hei 4(1992)-337459 bonds to RNAs in a cell. Therefore, Auramine O stains the cell membrane of erythrocytes only a little and the obtained fluorescence intensity is as little as those exhibited by other solid components such as crystals and yeast-like fungi, so that it was difficult to distinguish the erythrocytes from the other solid components when they are contained in the same sample. However, DiOCn(3) (n=1 to 6) bonds to and is adsorbed to all kinds of cell membrane and improves the stainability of erythrocytes and yeast-like fungi at the same time, thus making it possible to distinguish crystals, erythrocytes and yeast-like fungi by the difference of fluorescence intensity. Meanwhile, leukocytes are stained much more strongly than erythrocytes. Besides, improving stainability increases the fluorescence intensity, so that the influence of background fluorescence becomes small.

As a second fluorescent dye, a conventional dye known to stain damaged cells is used. Although the first dye can stain leukocytes, the stainability of damaged leukocytes is worse than that of living leukocytes and is on the same level as the fluorescence signal intensity of colonized bacteria, so that it was difficult to distinguish damaged leukocytes from these solid components when they are contained in the same sample. It has been found out that a dye such as EB which is capable of staining damaged cells can be used in order to compensate for the above-mentioned defects. By employing the second fluorescent dye, damaged leukocytes are stained more strongly than bacteria, making it possible to distinguish bacteria.

Further, it has been found out that the dyes capable of being excited by a red.wavelength light according to the present invention give results similar to those described above even if only one kind of dye is used.

Also, detection of urinary casts is facilitated by adjusting to the above range the electric conductivity of the reagent according to the present invention. Namely, it is desirable to measure the forward scattered light and the electric resistance signal to accurately detect urinary casts. In Japanese Unexamined Patent Publication No. Hei 4(1992)-337459, urinary casts are detected by measuring the forward scattered light and the forward fluorescent light. According to the method, urinary casts containing an inclusion body are detected, but hyaline casts were not sometimes detected so accurately when solid components other than urinary casts appear simultaneously in the specimen. In particular, it was difficult to distinguish hyaline casts and mucus threads because their fluorescence intensities are both very weak and their lengths are similar. However, hyaline casts and mucus threads can be accurately detected by further measuring the electric resistance signal as well as the forward scattered light and forward fluorescent light and combining the measurement parameters of scattered light pulse width (reflecting the length information) and the resistance pulse height value (reflecting the volume information). Urinary casts containing an inclusion body such as epithelial cast, granular cast, erythrocytic cast, leukocytic cast, etc. can be detected by combining the scattered light pulse width and the fluorescent light pulse width.

EXAMPLES

The reagent for analyzing solid components in urine according to the present invention and examples of methods for analyzing cells employing the reagent will be described hereinafter. However, they are not intended to limit the scope of the present invention.

Example 1

A diluent solution and a dyeing solution were prepared according to the prescription described below.

| •Diluent solution | | |
|---|---|---|
| Buffer agent | HEPES | 50 mM |
| | NaOH | in an amount to adjust pH at 7.0 |
| Osmotic pressure compensating agent | sodium propionate | in an amount to adjust osmotic pressure at 150 mOsm/kg |
| Chelating agent | EDTA-3K | 0.4 W/W % |
| The electric conductivity was 5 mS/cm. | | |
| •Dyeing solution | | |
| First dye | DiOC6(3) | 400 ppm |
| Second fluorescent dye | EB | 1600 ppm |
| Ethylene glycol was used as a solvent. | | |

Figure 2:
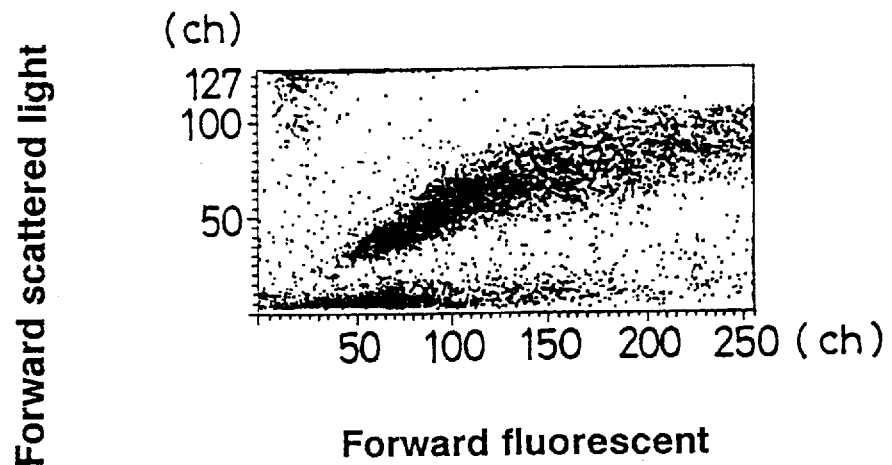
FIG. 2 is an enlarged view of FIG. 1.
Figure 3:
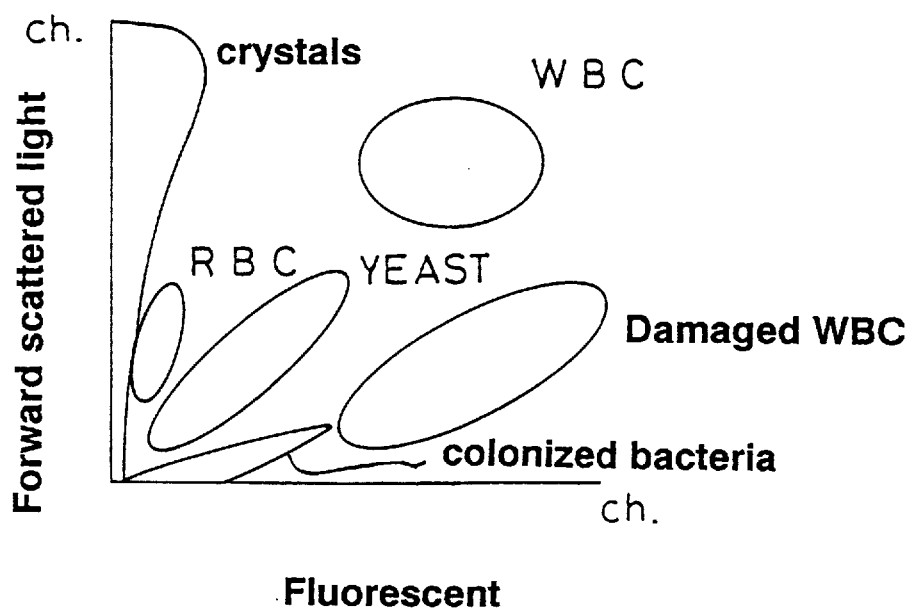
FIG. 3 is a model view of the scattergram obtained by measuring the forward scattered light and the forward fluorescent light when solid components in urine are stained by employing the reagent for analyzing solid components in urine according to the present invention.

Urine 400 μl was diluted in the above diluent solution 1160 μl and the above dyeing solution 40 μl was added (dilution ratio of 4) for staining at 35° C. for 10 seconds. The forward scattered light, the forward fluorescent light and the electric resistance signal were measured by a flow cytometer using an argon laser as a light source. Here, a side (90°) fluorescent light may be measured. FIGS. 1 and 2 show scattergrams obtained by measuring the forward scattered light and the forward fluorescent light using a specimen in which yeast-like fungi, leukocytes and erythrocytes appeared. As is clearly seen in FIGS. 1 and 2, yeast-like fungi, leukocytes, and erythrocytes are classified well when the reagent of the above Example is used. FIG. 3 shows a model view of the scattergram when solid components in urine are measured employing the reagent of the present invention.

Even when a specimen with background fluorescence was measured, the reagent of the above Example enabled measurements without being influenced by background fluorescence because cells were strongly stained.

Figure 4:
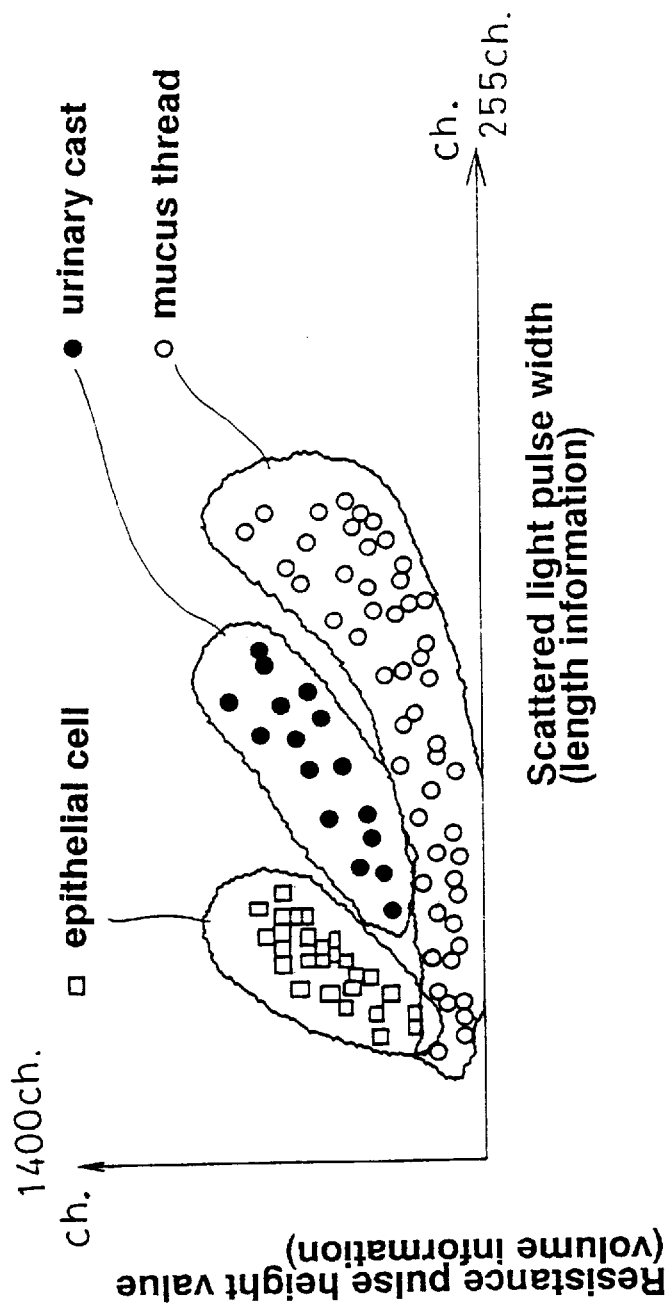
FIG. 4 is a model view of the scattergram illustrating the relation between the scattered light pulse width and the resistance pulse height value of the electric resistance signal measured after solid components in urine are stained by employing the reagent for analyzing solid components in urine according to the present invention.
Figure 5:
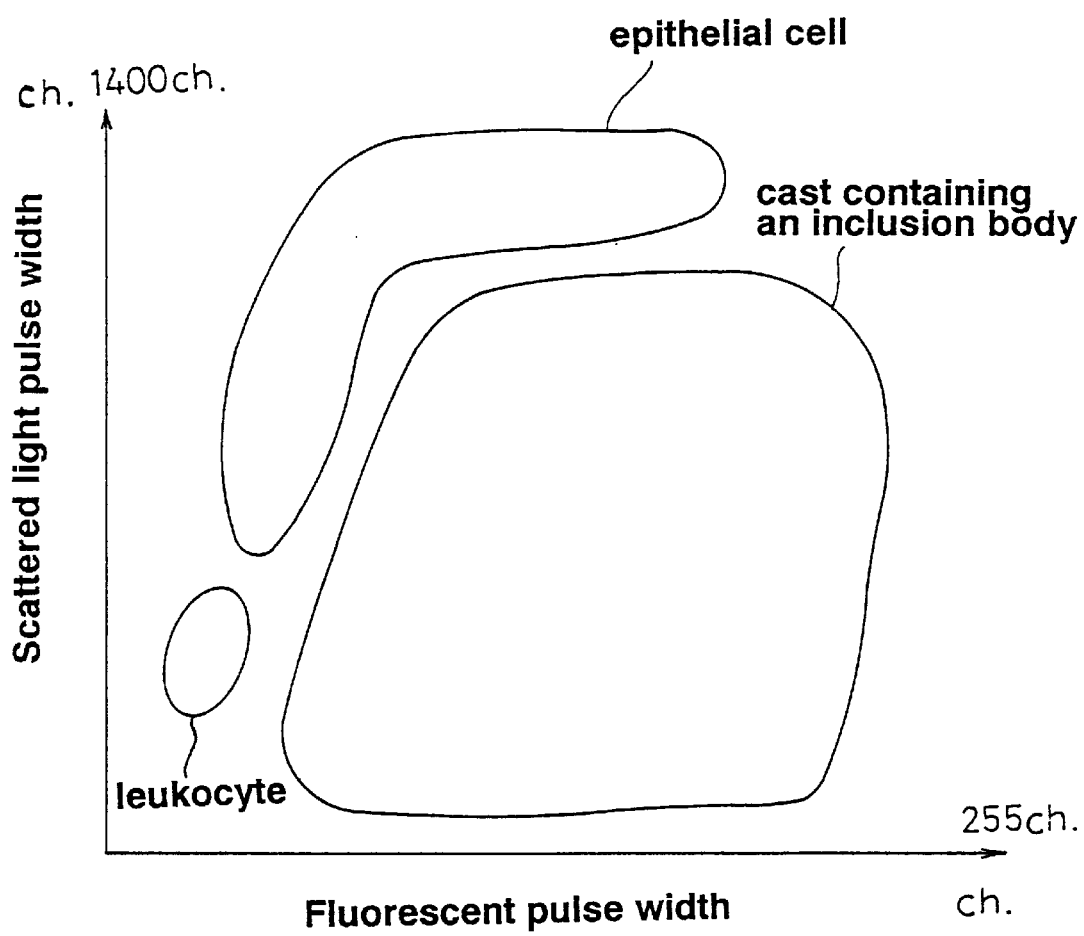
FIG. 5 is a model view of the scattergram illustrating the relation between the scattered light pulse width and the fluorescent light pulse width of the electric resistance signal measured after solid components in urine are stained by employing the reagent for analyzing solid components in urine according to the present invention.

Further, it was possible to detect and classify comparatively large solid components such as urinary casts (hyaline casts and urinary casts containing an inclusion body), mucus threads, epithelial cells by measuring electric resistance signals and observing the relation between the scattered light pulse width and the resistance pulse height value. A model view of the scattergram is shown in FIG. 4. Further, when urinary casts containing granules, erythrocytes, leukocytes and the like appeared, it was possible to measure the urinary casts more reliably by combining the fluorescent light pulse width with the scattered light pulse width. A model view of the scattergram is shown in FIG. 5.

Example 2

The reagent having the same composition as in the Example 1 was used and the same operations were repeated except that sodium propionate was added to adjust osmotic pressure to 210 mOsm/kg and the electric conductivity was 7 mS/cm.

The result was similar to that of the Example 1.

Example 3

The reagent having the same composition as in the Example 1 was used and the same operations were repeated except that sodium propionate was added to adjust osmotic pressure to 310 mOsm/kg and the electric conductivity was 10 mS/cm.

The result was similar to that of the Example 1.

Example 4

| •Diluent solution | | |
|---|---|---|
| Buffer agent | HEPES | 50 mM |
| | NaOH | in an amount to adjust pH at 7.0 |
| Osmotic pressure compensating agent | NaCl | in an amount to adjust osmotic pressure at 280 mOsm/kg |
| Chelating agent | EDTA-3K | 0.4 W/W % |
| •Dyeing solution | | |
| Dye | NK-529 | 800 ppm |
| Ethylene glycol was used as a solvent. | | |

Urine 400 μl was diluted in the above diluent solution 1184 μl and the above dyeing solution 16 μl was added for staining at 35° C. for 50 seconds. The forward scattered light and the side fluorescent light were measured by a flow cytometer using a red semiconductor laser as a light source. A scattergram similar to that of Example 1 was obtained.

Comparative Example 1

| •Diluent solution | | |
|---|---|---|
| Buffer agent (pH5.0) | citric acid | 27.6 mM |
| | sodium citrate | 22.4 mM |
| Osmotic pressure compensating agent | sodium propionate | in an amount to adjust osmotic pressure at 250 mOsm/kg |
| Chelating agent | EDTA-3K | 0.4 W/W % |
| The electric conductivity was 10.7 mS/cm. | | |
| •Dyeing solution | | |
| Dye | Auramine O | 30000 ppm |
| Ethylene glycol was used as a solvent. | | |

Ethylene glycol was used as a solvent.

Figure 7:
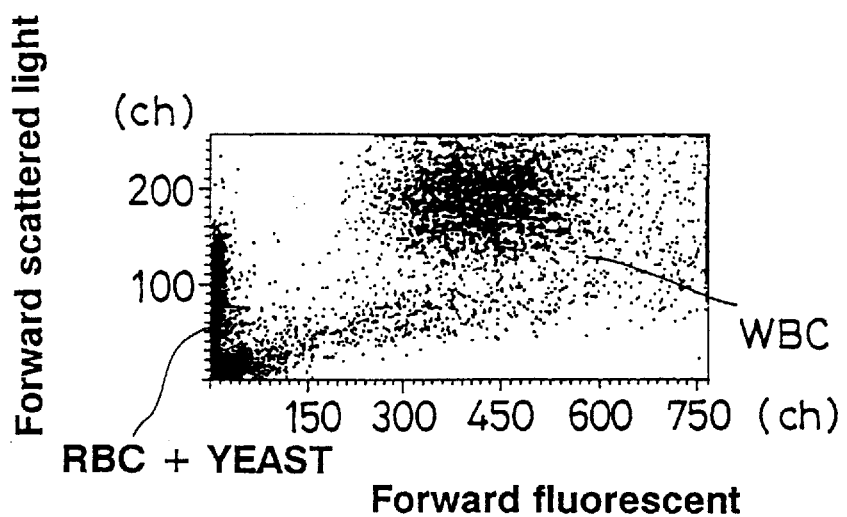
FIG. 7 is a scattergram obtained by measuring the forward scattered light intensity and the forward fluorescent light intensity when solid components in urine are stained by employing the reagent which contains auramine O for analyzing solid components in urine.
Figure 8:
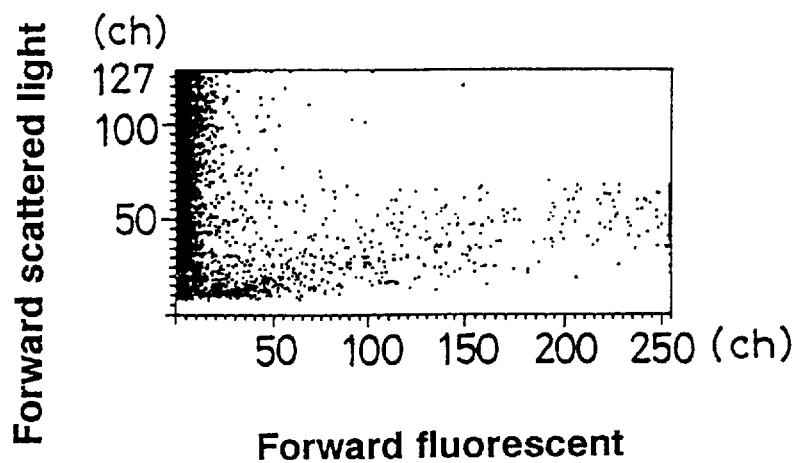
FIG. 8 is an enlarged view of FIG. 7.

Urine 400 μl was diluted in the above diluent solution 1160 μl and the above dyeing solution 40 μl was added (dilution ratio of 4) for staining at 35° C. for 10 seconds. The forward scattered light, the forward fluorescent light and the electric resistance signal were measured by a flow cytometer using an argon laser as a light source. FIGS. 7 and 8 show scattergrams obtained by measuring the forward scattered light and the forward fluorescent light. As is clearly seen in FIGS. 7 and 8, stainability of yeast-like fungi and erythrocytes was bad when the reagent of the above Comparative Example was used, so that it was impossible to distinguish them.

Figure 9:
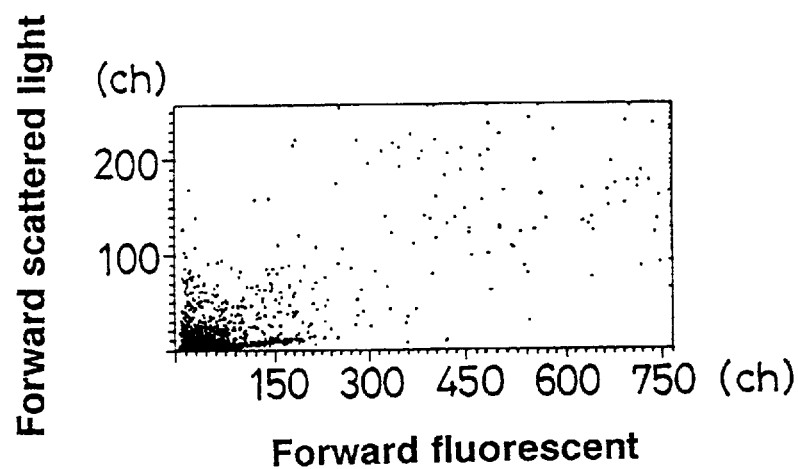
FIG. 9 is a scattergram obtained by measuring the forward scattered light intensity and the forward fluorescent light intensity when solid components in urine having background fluorescence are stained by employing the reagent which contains auramine O for analyzing solid components in urine.
Figure 10:
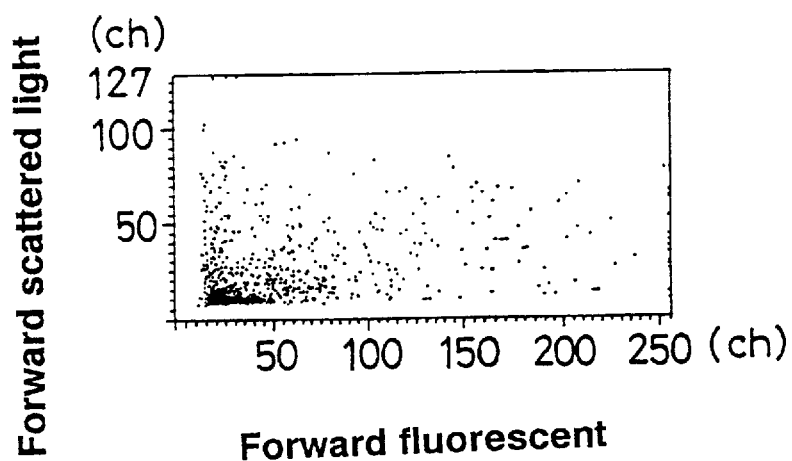
FIG. 10 is an enlarged view of FIG. 9.

Also, when a specimen having a background fluorescence was measured by using the reagent of the above Comparative Example, a region appeared in some part where measurement was totally impossible due to the influence of the background fluorescence, as is illustrated in FIGS. 9 and 10, rendering the analysis impossible.

When the forward scattered light and forward fluorescent light were measured in the above Example 1, the measurement was conducted with the detection sensitivity being about 16.6% as compared with Comparative Example 1. Therefore, it was confirmed that yeast-like fungi, leukocytes and erythrocytes can be classified well by using a detector with lower sensitivity. In other words, it is necessary to raise the detector sensitivity in Comparative Example 1 because the fluorescence from erythrocytes is very weak, whereas a detector with lower sensitivity can be used in the Example 1 of the present invention because erythrocytes also are stained strongly. Therefore, detector sensitivity for measurement can be lowered to such an extent that background fluorescence is almost negligible.

According to the reagent of the present invention for analyzing solid components in urine and the method of analyzing cells employing the reagent;
(1) The stainability of erythrocytes was improved and it has become possible to distinguish erythrocytes from crystals.
(2) The stainability of various solid components appearing in urine is improved, so that the sensitivity of photomultiplier tube (PMT) for detecting fluorescence can be reduced to such an extent that the influence of background fluorescence in urine itself is almost negligible.
(3) Even when many kinds of solid components appear simultaneously in urine, it is possible to distinguish them more accurately.
(4) The ability of distinguishing urinary casts has been improved.

What is claimed is;:

1. A method capable of differentiating at least crystalline components, erythrocytes, yeast-like fungi and leukocytes in urine which comprises the steps of:

mixing the urine with a reagent for analyzing solid components in urine comprising:
(i) a buffer agent for maintaining pH at 5.0 to 9.0,
(ii) an osmotic pressure compensating agent for maintaining osmotic pressure at 100 mOsm/kg to 600 mOsm/kg,
(iii) a first dye which is a condensed benzene derivative selected from the group consisting of the following formula:
3,3'-(di-n-hexyl)-2,2'-oxacarbocyanine iodide (NK-2280, DiOC6(3))

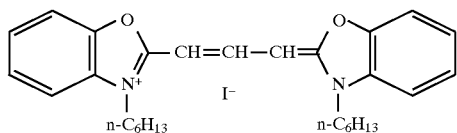

2-(p-dimethylaminostyryl)-3-methylbenzooxazolium iodide (NK-528)

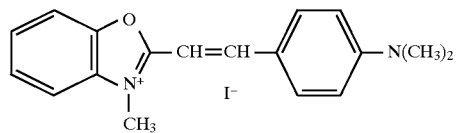

2-(p-dimethylaminostyryl)-1,3,3-trimethyl-3H-indolium iodide (NK-97)

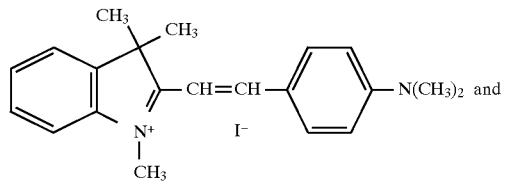

Basic Red 14

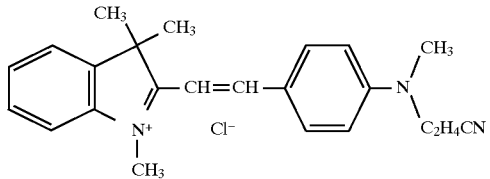

and is capable of differentiating crystalline components, erythrocytes and yeast-like fungi,
(iv) a second fluorescent dye capable of staining a damaged cell, and
(v) a chelating agent to stain the desired solid components in the urine, applying an excitation light to solid components in the above stained urine, and measuring the scattered light and the fluorescent light emitted from the solid components.

2. A method according to claim 1, wherein an electric resistance signal is measured after the solid components in the urine are stained.

3. A method according to claim 1, wherein the reagent for analyzing is mixed with the urine after the reagent is previously warmed.

4. A method according to claim 1, wherein said buffer agent maintains pH at 6.5 to 7.5.

5. A method according to claim 4, wherein said buffer agent maintains pH at 6.8 to 7.2.

6. A method according to claim 1, wherein said osmotic pressure compensating agent maintains osmotic pressure at 150 mOsm/kg to 500 mOsm/kg.

7. A method according to claim 1, wherein the electrical conductivity of the reagent is adjusted to 1 to 10 mS/cm.

8. A method according to claim 7, wherein the electrical conductivity of the reagent is adjusted to 4 to 7 mS/cm.

9. A method according to claim 1, wherein the reagent for analyzing is previously warmed to 30° C. to 40° C.

10. A method according to claim 9, wherein the reagent for analyzing is previously warmed to 33° C. to 37° C.

11. A method capable of differentiating at least crystalline components, erythrocytes, yeast-like fungi and leukocytes in urine which comprises the steps of:

mixing the urine with a reagent for analyzing solid components in urine comprising:
(I) a buffer agent for maintaining pH at 5.0 to 9.0,
(II) an osmotic pressure compensating agent for maintaining osmotic pressure at 100 mOsm/kg to 600 mOsm/kg,
(III) a dye capable of being excited by a red wavelength light, which is selected from the group consisting of the following:

NK-321
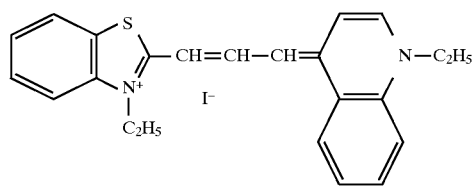
NK-1590
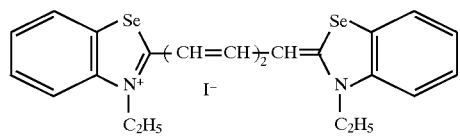
NK-529
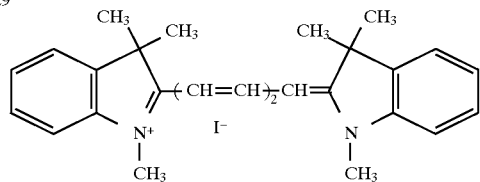
NK-2780
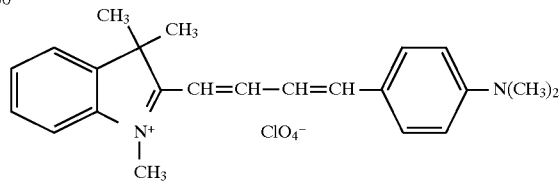
NK-2782
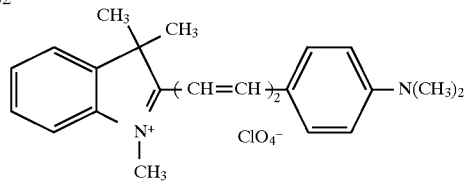
Oxazine 4
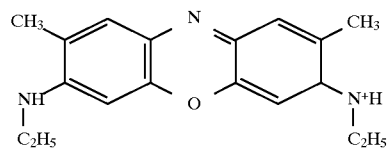
NK-138
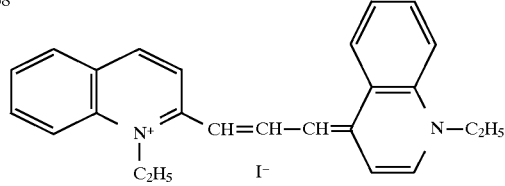

-continued
Basic Green
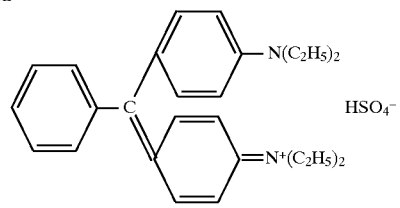
Capri Blue GON
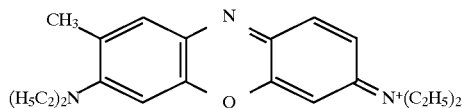
Basic Green 4
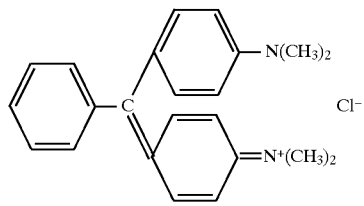
NK-2783
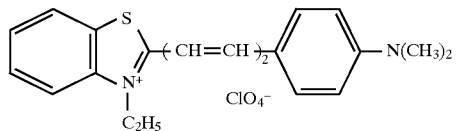
Basic Blue 1
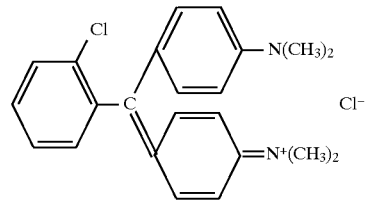
NK-375
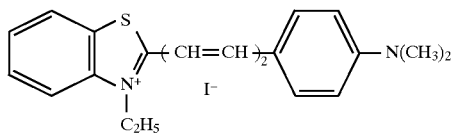
Oxazine 750 perchlorate
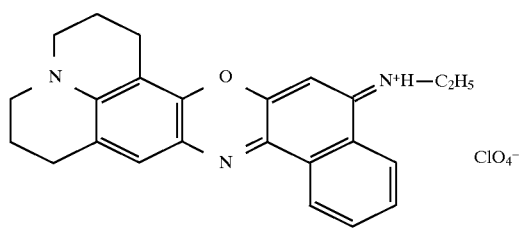

NK-1954
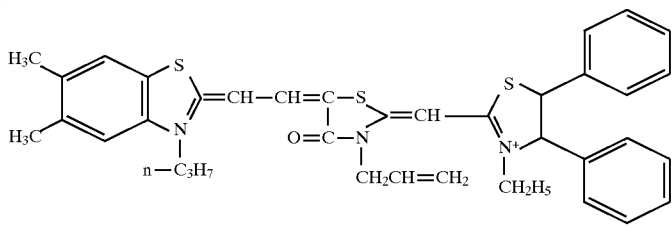
Basic Blue 20
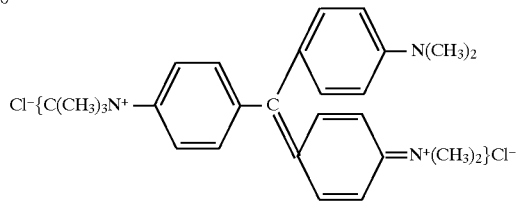
Basic Blue 24
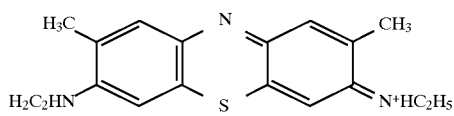
Oxazine 720
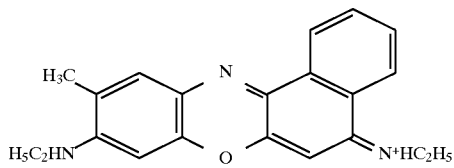
NK-1836
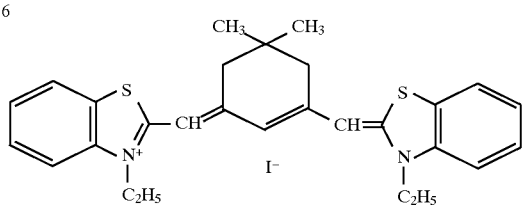
NK-136
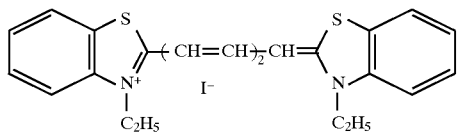
NK-1511
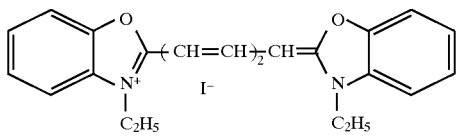
NK-376
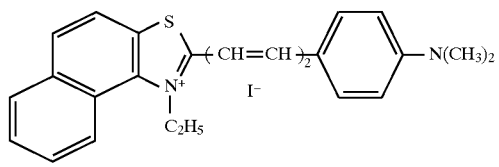

NK-2711

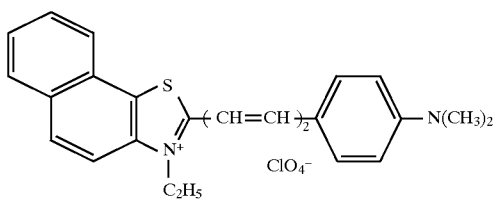

Iodine Green

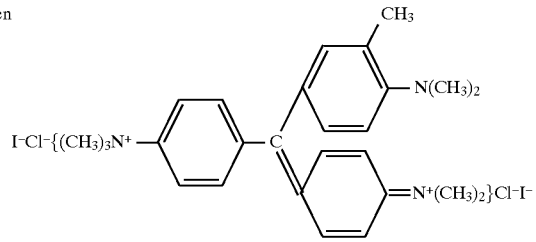

NK-96

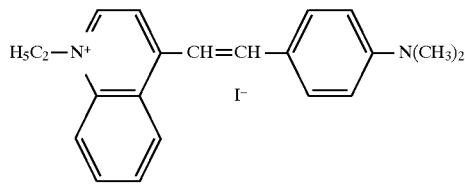

Rhodnile Blue, Capri Blue BB, Basic Blue 124 and Basic Blue 1, and is capable of differentiating crystalline components, erythrocytes and yeast-like fungi, and (IV) a chelating agent to stain the desired solid components in the urine, applying an excitation light to solid components in the above stained urine, and measuring the scattered light and the fluorescent light emitted from the solid components.

12. A method according to claim 11, wherein an electric conductivity signal is measured after the solid components in the urine are stained.

13. A method according to claim 11, wherein the reagent for analyzing is mixed with the urine after the reagent is previously warmed.

14. A method according to claim 2, wherein said buffer agent maintains pH at 6.5 to 7.5.

15. A method according to claim 14, wherein said buffer agent maintains pH at 6.8 to 7.2.

16. A method according to claim 11, wherein said osmotic pressure compensating agent maintains osmotic pressure at 150 mOsm/kg to 500 mOsm/kg.

17. A method according to claim 11, wherein the electrical conductivity of the reagent is adjusted to 1 to 10 mS/cm.

18. A method according to claim 17, wherein the electrical conductivity of the reagent is adjusted to 4 to 7 mS/cm.

19. A method according to claim 11, wherein the reagent for analyzing is previously warmed to 30° C. to 40° C.

20. A method according to claim 19, wherein the reagent for analyzing is previously warmed to 33° C. to 37° C.

* * * * *